(12) United States Patent
Wang

(10) Patent No.: US 11,079,390 B2
(45) Date of Patent: Aug. 3, 2021

(54) METHODS AND COMPOSITIONS FOR MASS SPECTROMETRY ANALYSIS

(71) Applicant: Tianxin Wang, Walnut Creek, CA (US)

(72) Inventor: Tianxin Wang, Walnut Creek, CA (US)

( * ) Notice: Subject to any disclaimer, the term of this patent is extended or adjusted under 35 U.S.C. 154(b) by 0 days.

(21) Appl. No.: 16/253,142

(22) Filed: Jan. 21, 2019

(65) Prior Publication Data
US 2019/0170764 A1 Jun. 6, 2019

Related U.S. Application Data

(63) Continuation of application No. 15/227,966, filed on Aug. 4, 2016, now abandoned, which is a continuation-in-part of application No. 13/385,391, filed on Feb. 17, 2012, now abandoned, which is a continuation-in-part of application No. 12/456,786, filed on Jun. 23, 2009, now Pat. No. 8,119,416, which is a continuation-in-part of application No. 10/755,986, filed on Jan. 13, 2004, now Pat. No. 7,550,301.

(60) Provisional application No. 60/439,631, filed on Jan. 13, 2003.

(51) Int. Cl.
*G01N 33/68* (2006.01)
*H01J 49/16* (2006.01)

(52) U.S. Cl.
CPC ........ *G01N 33/6851* (2013.01); *H01J 49/164* (2013.01); *G01N 2560/00* (2013.01); *Y10T 436/24* (2015.01)

(58) Field of Classification Search
None
See application file for complete search history.

(56) References Cited

U.S. PATENT DOCUMENTS

| | | |
|---|---|---|
| 5,719,060 A | 2/1998 | Hutchens |
| 5,952,654 A | 9/1999 | Giese |
| 6,093,541 A | 7/2000 | Nelson |
| 6,316,266 B1 | 11/2001 | Nelson |
| 7,550,301 B2 | 6/2009 | Wang |
| 8,119,416 B2 | 2/2012 | Wang et al. |
| 2012/0208295 A1 | 8/2012 | Wang |
| 2017/0212128 A1 | 7/2017 | Wang |

OTHER PUBLICATIONS

Short, L.C. et al. Electrospray photoionization (ESPI) liquid chromatography/mass spectrometry for the simultaneous analysis of cyclodextrin and pharmaceuticals and their binding interactions, Rapid Communications in Mass Spectrometry, 22, 541-548 (Year: 2008).*

(Continued)

*Primary Examiner* — Xiaoyun R Xu

(57) ABSTRACT

Methods and compounds are provided to improve the desorption and ionization of analyte for mass spectrometry analysis. More specifically, it is for electrospray ionization (ESI) mass spectrometry. The method uses charged affinity molecules that can bind with analyte either temporarily or permanently to improve the desorption and ionization of analyte. The charged affinity molecules can be positively charged or negatively charged.

5 Claims, 15 Drawing Sheets

(56) References Cited

OTHER PUBLICATIONS

Zia, V. et al. Effect of Cyclodextrin Charge on Complexation of Neutral and Charged Substrates: Comparison of (SBE)7M-b-CD to HP-b-CD, Pharmaceutical Research, vol. 18, No. 5, 667-673 (Year: 2001).*

Galaverna, G. et al. Histamine-modified cationic b-cyclodextrins as chiral selectors for the enantiomeric separation of hydroxy acids and carboxylic acids by capillary electrophoresis, Electrophoresis, 20, 2619-2629 (Year: 1999).*

Ian W. Wymana Donal H. Macartney Cucurbit[7]uril host—guest complexes of cholines and phosphonium cholines in aqueous solution Drg. Biomol. Chem., 2010,8, 253-260.

Galaverna G1, Corradini R, Dossena A, Marchelli R. Electrophoresis. Sep. 1999;20(13):2619-29.

de Fátima A, Fernandes SA, Sabino AA. Calixarenes as new platforms for drug design. Curr Drug Discov Technol. Jun. 2009;6(2):151-70.

Alexandre Specht, Fabio Ziarelli, Philippe Bernard, Maurice Goeldnera and Ling Peng para-Sulfonated Calixarenes Used as Synthetic Receptors for Complexing Photolabile Cholinergic Ligand Helvetica Chimica Acta—vol 88 (2005) 2641-53.

D'Urso A, Cristaldi DA, Fragala ME, Gattuso G, Pappalardo A, Villari V, Micali N, Pappalardo S, Parisi MF, Purrello R. Sequence, Stoichiometry, and Dimensionality Control in Porphyrin/Biscalix[4]arene Self-Assemblies in Aqueous Solution Chemistry. Sep. 10, 2010;16(34):10439-4.

\* cited by examiner

METHODS AND COMPOSITIONS FOR MASS SPECTROMETRY ANALYSIS

CROSS-REFERENCE TO RELATED APPLICATIONS

This is a Continuation application of U.S. application Ser. No. 15/227,966, filed Aug. 4, 2016, which is a Continuation-In-Part application of U.S. application Ser. No. 13/385,391, filed Feb. 17, 2012, which is a Continuation-In-Part application of U.S. application Ser. No. 12/456,786, filed Jun. 23, 2009 now U.S. Pat. No. 8,119,416, which is a Continuation-In-Part application of U.S. application Ser. No. 10/755,986, filed Jan. 13, 2004 now U.S. Pat. No. 7,550,301, which claims priority to U.S. Provisional Application No. 60/439,631, filed on Jan. 13, 2003. The disclosures of which are incorporated herein by reference in their entirety.

BACKGROUND OF THE INVENTION

Field of the Invention

This invention relates to methods and compounds to improve the desorption and ionization of analyte for mass spectrometry analysis. More specifically, this invention relates to the field of mass spectrometry, especially to the type of matrix-assisted laser desorption/ionization used to analyze macromolecules, such as proteins or biomolecules. Most specifically, this invention relates to the method of using photon energy absorbing molecules that can bind with analyte either temporarily or permanently to improve the desorption and ionization of analyte.

This invention also provides methods and compounds to improve the desorption and ionization of analyte for electrospray ionization (ESI) mass spectrometry analysis. The method uses charged affinity molecules that can bind with analyte either temporarily or permanently to improve the desorption and ionization of formed analyte complex. The charged affinity molecules can be positively charged or negatively charged.

Background Information

This invention relates generally to methods and compounds for desorption and ionization of analytes for the purpose of subsequent scientific analysis by such methods, for example, as mass spectrometry (MS) or biosensors. Generally, analysis by mass spectrometry involves vaporization and ionization of a small sample of material, using a high energy source, such as a laser, including a laser beam. Certain molecules that can absorb the photon energy of laser beam can be added to the sample to aid the desorption and ionization of analytes. These photon absorbing molecules are called matrix. The material is vaporized from the surface of a probe tip into the gas or vapor phase by the laser beam, and, in the process, some of the individual molecules are ionized. The positively or negatively charged ionized molecules are then accelerated through a short high voltage field and let fly (drift) preferably into a high vacuum chamber, at the far end of which they strike a sensitive detector. In some mass spectrometry method, such as ion mobility spectrometry, atmosphere pressure instead of high vacuum is used. Since the time-of-flight is a function of the mass of the ionized molecule, the elapsed time between ionization and impact can be used to determine the molecule's mass which, in turn, can be used to identify the presence or absence of known molecules of specific mass. Besides using time-of-flight, other methods such as ion trap also can be used to detect the mass and intensity of ion. Matrix-assisted laser desorption/ionization (MALDI) mass spectrometry has become a very important tool of modern chemistry and biotechnology. It is highly desirable that certain analyte molecules can be selectively desorbed and ionized to reduce signal peak interference and improve detection sensitivity.

A patent search was conducted to examine the means for reducing signal peak interference and improved detection sensitivity for mass spectrometry. The following prior art patents were located in the course of the patent search, and are considered to be the references most pertinent to the invention.

The Nelson U.S. Pat. No. 6,093,541, issued on Jul. 25, 2000 illustrates a mass spectrometer having a derivatized sample presentation apparatus;

The Nelson U.S. Pat. No. 6,316,266 issued on Nov. 13, 2001 illustrates a sample presentation apparatus for mass spectrometry;

The Hutchens U.S. Pat. No. 5,719,060 issued on Feb. 17, 1998 illustrates methods and apparatus for desorption and ionization of analytes for the purpose of subsequent scientific analysis by such methods;

The Giese; Roger U.S. Pat. No. 5,952,654 issued on Sep. 14, 1999 illustrates a field-release mass spectrometry methods of releasing and analyzing substrates such as DNA;

All the prior art patents examined involve modifying the sample presentation probe to selectively bind with certain analyte molecules and washing away the unbound analyte for improved detection. None of the prior art patents used modified matrix that can selectively form covalent or non-covalent interaction with certain analyte to improve their desorption and ionization. These methods involves heterogeneous binding, intensive washing, therefore are labor intensive, time consuming and may result in loss of analytes. They improve the detection of desired analyte indirectly by washing away interference molecules in the sample to decrease the noise and can not directly increase the desorption and ionization of desired analyte. The method in our invention is primarily directed towards direct increasing the desorption and ionization of desired analyte by forming a photon energy absorbing molecules-desired analyte complex for mass spectrometry analysis.

SUMMARY OF THE INVENTION

An object of the invention is to provide improved methods and materials for desorption and ionization of multiple or selected analytes into the gas (vapor) phase.

Another object is to provide means to selectively enhance the desorption/ionization of analyte molecules by using photon energy absorbing molecules that carry certain affinity groups.

A further object is to provide means to selectively enhance the desorption/ionization of analyte molecules by using photon energy absorbing molecules that carry certain reactive groups.

Yet another object is to provide methods and compounds to improve the desorption and ionization of analyte for mass spectrometry analysis. More specifically, it is for electrospray ionization (ESI) mass spectrometry. The method uses charged affinity molecules that can bind with analyte either temporarily or permanently to improve the ionization of analyte. The charged affinity molecules can be positively charged or negatively charged. This method improves the electrospray ionization of non-ionizable analyte.

Other and further objects, features and advantages will be apparent and the invention will be more readily understood from a reading of the following specification and by reference to the accompanying drawings forming a part thereof, wherein the examples of the present preferred embodiments of the invention are given for the purposes of disclosure.

DESCRIPTION OF THE INVENTIONS AND THE PREFERRED EMBODIMENT

Figure 1:
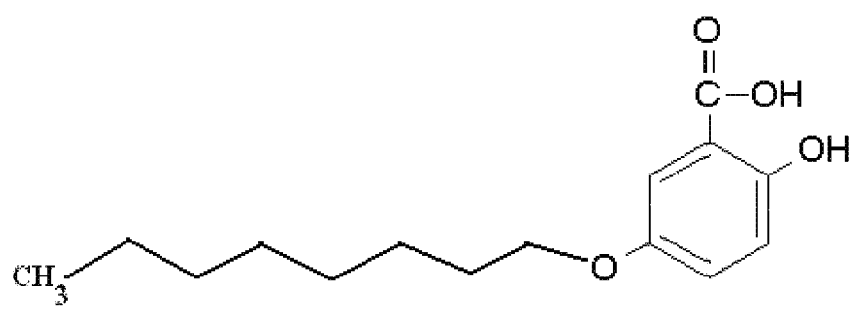
FIG. 1 shows an example of the selective affinity matrix.

Matrix for MALDI (matrix-assisted laser desorption/ionization mass spectrometry) is photon energy-absorbing molecules that can absorb energy from laser pulse and then push the analyte nearby into gas phase for mass analysis. Currently, most matrix molecules are small organic molecule such as DHB (2,5-dihydroxy benzoic acid) and sinapinic acid, which cannot selectively desorb/ionize molecules from a complex mixture of analytes. These matrix molecules also can not selectively bind with analyte either covalently or non-covalently. To perform the mass spectrometry analysis, matrix is mixed with the sample containing analyte and then added onto the probe; the probe is then inserted into the MALDI mass spectrometer for the analysis.

In the current invention, photon energy absorbing molecules that can bind with certain analyte either temporarily or permanently are added to the sample solution to form an analyte-photon energy absorbing molecules complex during mixing and incubation; the resulting solution is then added onto the probe and the probe is inserted into the MALDI mass spectrometer for analysis. This kind of photon energy absorbing molecules are essentially matrix that can bind with analyte covalently or non-covalently, therefore are called binding matrix or affinity matrix. In some embodiments, these binding matrix molecules comprise two parts conjugated together: a photon energy absorbing moiety and a binding moiety. The binding moiety can be reactive groups that can form covalent bond with target molecules. Alternatively, a carrier moiety or linker moiety is used to connect the photon energy absorbing moiety and the binding moiety. The carrier or linker can be either small molecule or polymer or any other chemical entity can be used as a carrier/linker as long as it has multiple functional groups that allow direct or indirect conjugation of the photon energy absorbing moiety and the binding moiety. Appropriate natural or synthetic polymers include, but are not limited to, oligomers (such as peptides), linear or cross linked polymers (such as polylysine, polyacrylic acid, proteins) or highly branched macromolecules (such as dendrimers). The photon energy absorbing moiety can be matrix currently used or any other chemical entities that have strong photon energy absorbing capability. More than one photon energy absorbing unit and more than one binding unit can be incorporated in one unit of the binding matrix.

The photon energy absorbing molecules in the current invention include but not limited to the matrix molecules currently used in MALDI analysis such as cinnamamide, 2,5-dihydroxybenzoic acid and alpha-cyano-4-hydroxycinnamic acid. The photon energy absorbing molecules/moiety further includes molecules that can strongly absorb the photon energy from IR, UV or visible light. Preferably these molecules should have a strong absorption for the light source used in the MALDI analysis. A skilled in the art can readily find many molecules and chemical moieties that have strong absorption for certain wavelength of photon. The chemical structures of strong photon energy absorbing molecules and chemical moieties are well known to the skilled in the art and can be readily found in the textbook of absorption spectrometry analysis. For example, aromatic compound and conjugated hetero cycles normally have strong UV absorption for UV light, especially when coupled with auxochrome. The chromophore and auxochrome in UV and visible light range are well known and the absorption band can be readily calculated from its chemical structure and adjusted by changing the chemical structure.

The binding could be either reactivity based covalent binding or affinity based non-covalent binding. Because matrix molecules absorb and transfer the energy to the molecules adjacent to them, selective binding of analytes to the matrix molecules can selectively desorb/ionize the analytes.

For non-covalent binding, the binding moieties are chemical entities with affinity groups/moieties having affinity for the analyte to be detected. The affinity group/moiety or groups/moieties can be any chemical or biological functionality with affinity for certain analytes. There are many molecules having chemical or biological functionality with affinity for analyte. These molecules or their affinity moiety can be used as binding moieties in the current invention. They include, but are not limited to, DNA, PNA (peptide nucleic acid), polynucleotides, antibody, antigen, aptamers, chelator, metals, lipophilic structures or molecules, hydrophilic structures or molecules, ionic structures or molecules (such as acidic and basic molecules), dendrimer, polymers having affinity groups and other structures having specific affinity interactions with certain analytes. Through the binding between the affinity group/moiety and the analyte, the non-covalent interaction between the matrix and the specific analyte will enable the matrix selectively desorb/ionize these analytes for mass analysis. This type of matrix can be called affinity matrix. In some embodiments the photon-absorbing moiety is coupled directly to the affinity group/moiety. In other embodiments the photon-absorbing moiety is coupled to the affinity group/moiety though a linker/spacer. In some embodiments one affinity moiety is coupled with multiple photon-absorbing moieties.

The resulting mass detected could either be the mass of the analyte or the mass of analyte plus matrix based on the strength of the affinity. These novel matrix molecules could be used either alone or in combination with known matrix. This new method is useful in both single analyte detection and analytes pattern profiling such as protein pattern profiling for diagnosis, biomarker discovery and proteomic study. If multiple these kinds of affinity matrix molecules are used for a sample containing multiple analytes, multiple analytes can be selectively detected simultaneously. Compared with other protein chip technologies and MALDI methods, this method provides a more sensitive and convenient solution.

For covalent binding, the binding moiety can be any chemical entities having certain reactive groups that can covalently couple to the analyte to be detected upon incubation, therefore these binding matrix molecules are indeed reactive matrix. The reactive groups include, but are not limited to anhydride, active ester, aldehyde, alkyl halide, acid chloride, isothiocyanate and other reactive groups that can react with functional group such as amine, hydroxyl, SH or other groups on the analyte molecules. Examples of active ester include but not limited to NHS ester, HOBt ester, HOAt ester, pentafluorophenyl ester and p-nitrophenyl ester. A skilled in the art can readily find more reactive groups from the textbook of organic synthesis. Upon mixing them together, the analyte molecules are covalently coupled with these reactive groups of the reactive matrix, and the masses detected are those of adducts formed by the analyte molecules and the matrix. The desorption/ionization of certain molecules can thus be enhanced, and the mass spectra will exhibit a unique pattern of mass of derivatives which gives clues to structure of the molecules. These novel matrix molecules can be used either alone or in combination with known matrix.

It is well known that anhydride, active ester, aldehyde, alkyl halide, acid chloride can readily react with the target molecule's amine groups and hydroxyl, SH groups. One can easily find more reactive groups for certain functional groups in the target molecules in the text book of organic chemistry. The incubation can be done in either in organic or non-organic solvent depending on the solubility and reactivity of the reagents and analyte. In some embodiments the reactive group is conjugated directly to the photon-absorbing moiety. In other embodiments the reactive group is part of the photon-absorbing moiety. Yet in another embodiments the photon-absorbing moiety is coupled to the reactive group though a linker or spacer.

For example, a reactive matrix is a photon-absorbing molecule having a reactive group anhydride. In an analyte, there are molecules containing amine or —OH functionality, and molecules not containing amine functionality and —OH groups. When this reactive matrix is mixed with the analyte, its anhydride group reacts with amine or —OH to form covalent amide/ester bond, leaving molecules without amine/—OH group intact. If the molecule has 3 amine groups, some of them will react with one, two, and three matrix molecules respectively, and exhibit a series of masses of target molecule plus one, two and three photon-absorbing moiety in the spectra. By this method, the desorption/ionization of the molecule is selectively enhanced, and the mass pattern gives clues to its structural information.

Alternatively, pseudo-reactive matrix molecules can also be employed. A pseudo-matrix molecule is not a matrix by it self and can not absorb photon energy. It has a reactive group such as anhydride, aldehyde, alkyl halide, acid chloride, and other reactive groups that can react with functional group such as amine, hydroxyl, SH or other groups on the analyte molecules. When its reactive group reacts with a functional group and form a covalent bond, the resulting coupling product becomes capable of absorbing photon energy and performing desorption/ionization activity.

Further more, the photon energy absorbing molecules described above can have charged groups. After binding with analyte molecules, the formed product complex (either covalent or non-covalent) will carry the charged groups. These charged groups improve the ionization of the analyte complex and therefore improve the sensitivity of the MALDI analysis. The charged groups can be positively charged if MALDI is set to detect positive ion or be negatively charged in MALDI is set to detect negative ion. Preferably, the charged groups are strongly ionizable groups such as tertiary amine or quaternary amine for positive ions and phosphoric acid groups and sulphonic groups for negative ions. It is desirable that these charged groups are permanently charged, e.g. quaternary amine. In some embodiments the charged group is conjugated to the photon-absorbing moiety. In other embodiments the changed group is part of the photon-absorbing moiety. Yet in another embodiments the photon-absorbing moiety is coupled to the charged group though a linker or a spacer.

Formula I shows an example of a charged affinity matrix used in some embodiments, which is essentially an affinity matrix described above having a charged group R. Here the affinity group is AB, which is an antibody having specific affinity to certain antigen. The charged group R is a functional group having a positive charge, such as a $(CH_3)_3N^+$—$CH_2$—O— group. This matrix is used for the detection of antigen specific to AB.

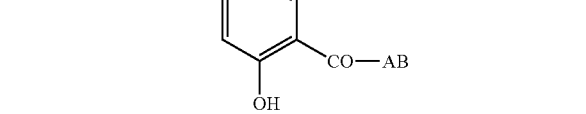

I

Formula II shows an example of a charged reactive matrix used in some embodiments, which is essentially a reactive matrix described above attached with a charged group R. Here the reactive group is X, such as an acid or active ester group or an anhydride group that can react with amine group or —OH group of the analyte readily. The charged group R is a functional group having a positive charge, such as a $(CH_3)_3N^+$—$CH_2$—O— group, or a guanidino group for positive ion MALDI, or a functional group having a negative charge, such as a —$CH_2OP(OH)_2OO^-$ group for negative ion MALDI.

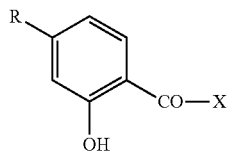

Because only the charged analyte can be detected in MALDI and ESI, therefore, aid in giving analyte charges can also enhance the sensitivity of MALDI and ESI. Charged affinity molecules that can specific bind with certain analyte would form a charged complex with the analyte molecule: charged affinity molecule plus analyte when mix them together. This charged complex can be easily detected and have high detection sensitivity since it is already charged. Therefore one can detect the analyte molecule easily by adding charged affinity molecule to the sample containing the analyte and detecting the complex formed by charged affinity molecule plus analyte in varieties of mass spectrometry methods. The high detecting sensitivity of the complex enables one to detect the specific analyte sensitively and selectively. Many markers that have unique patterns in mass spectrometry such as the bromine can be incorporated into the charged affinity molecule to aid the discrimination of the complex. In some embodiments the charged affinity molecules do not need to have the matrix effect. The mass detected is the mass of charged affinity molecule plus analyte. The formation of the detectable complex relies on the strong binding between the charged affinity molecule and the analyte. In one embodiment, Biotin is a small molecule that can bind with streptavidin tightly. $(CH_3)_3N^+$—$CH_2$—$NH_2$ is couple with the —COOH in biotin giving amide bond to form a charged affinity molecule for streptavidin detection. Upon mixing them together, the detection of streptavidin will be enhanced due to the formed charged biotin+streptavidin complex in MALDI or ESI. A non acidic matrix is preferred when using MALDI as the mass spectrometry method.

Since these affinity molecules do not need to have matrix effect, their application is not limited in MALDI, they can be used in any mass spectrometry analysis methods, such as electron impact (EI), fast atom bombardment (FAB), electrospray ionization (ESI), chemical ionization CI, field ionization (FI), field desorption (FD) and etc. The detect MW will be the adduct of the affinity molecule with analyte.

Electrospray ionization (ESI) is a technique used in mass spectrometry to produce ions. It is especially useful in producing ions from macromolecules because it overcomes the propensity of these molecules to fragment when ionized. In ESI, the liquid containing the analyte(s) of interest is dispersed by electrospray into a fine aerosol. The ions observed by mass spectrometry may be ions created by the addition of a proton (a hydrogen ion) and denoted $[M+H]^+$, or of another cation such as sodium ion, $[M+Na]^+$, or the removal of a proton, $[M-H]^-$. Multiply charged ions such as $[M+nH]^{n+}$ are often observed. For large macromolecules, there can be many charge states, resulting in a characteristic charge state envelope. All these are even-electron ion species: electrons (alone) are not added or removed, unlike in some other ionization sources. The analyte are sometimes involved in electrochemical processes, leading to shifts of the corresponding peaks in the mass spectrum. Electrospray ionization is the ion source of choice to couple liquid chromatography with mass spectrometry. The analysis can be performed online, by feeding the liquid eluting from the LC column directly to an electrospray, or offline, by collecting fractions to be later analyzed in a classical nanoelectrospray-mass spectrometry setup.

However, if the analyte is not ionizable or difficult to be ionized, it will be difficult to get the ion peak for detection in ESI. The current invention provide a method to solve this problem by mixing the sample containing the analyte with a charged affinity molecule, which can bind with the analyte to form a noncovalently bound complex between said analyte and said charged affinity molecule, which in turn can be detected by ESI. The current method is especially suitable for detecting and analyzing non-ionizable analyte (e.g. those have no amine or acid groups), it will help the ionization of these non-ionizable analyte in the form of a charged ionizable binding complex formed between the non-ionizable analyte and the charged affinity molecule.

The disclosed method to detect analyte molecules using electrospray ionization (ESI) mass spectrometry comprise: providing charged affinity molecule having charged moiety and affinity moiety that can bind with said analyte molecule via a non-covalent bond or covalent bond; mixing said charged affinity molecules with a sample solution containing said analyte to form a solution containing a covalently bound complex or a noncovalently bound complex between said analyte and said charged affinity molecule; performing electrospray ionization (ESI) mass spectrometry for the solution containing the bound complex, and detecting the presence of the analyte by detecting the presence of the bound complex in mass spectrometry. The charged group can be either positively charged group or negatively charged group. The affinity moiety can be selected from antibody, antigen, aptamer, polynucleotides, chelators, metals, lipophilic molecules, hydrophilic molecules, host molecules and ionic molecules. For small molecule analyte, the host molecule for the analyte molecule used in host-guest chemistry can be selected, such as cyclodextrins, calixarenes, cucurbiturils, pillararenes, porphyrins, metallacrowns, crown ethers, zeolites, cyclotriveratrylenes, cryptophanes, carcerands and their analogues or derivatives.

In some embodiments, these charged affinity molecules comprise two parts conjugated together: a charged moiety (the term charged moiety in the current invention also include those highly ionizable moiety, which may be in neutral state but can become charged readily, the term charged include highly ionizable) and a binding moiety. The binding moiety can also be reactive chemical group that can form covalent bond with target molecule as previously described. In other embodiments, a carrier moiety or linker moiety or spacer is used to connect the charged moiety and the binding moiety. The term linker/spacer is well known in bio conjugation and crosslinking chemistry, which can be found readily in publications and literatures. The carrier or linker or spacer can be either small molecule and its fragment (e.g. the hydroxybenzoic acid in formula I, amino acid, short PEG, alkyl chain, amide bond, ester bond, disulfide bond and etc.) or polymer or any other chemical entity can be used as a carrier/linker as long as it has multiple functional groups that allow direct or indirect conjugation of the charged moiety and the binding moiety. Appropriate natural or synthetic polymers include, but are not limited to, oligomers (such as peptides), linear or cross linked polymers (such as polylysine, polyacrylic acid, proteins) or highly branched macromolecules (such as dendrimers). In some embodiments, the affinity moiety is the charged moiety by itself. For non-covalent binding, the binding moiety is chemical entity with affinity group having affinity for the analyte to be detected. The binding moiety, affinity group/ groups can be any chemical or biological functionality with affinity for certain analyte. They include, but are not limited to, DNA, PNA (peptide nucleic acid), polynucleotides, antibody, antigen, aptamers, chelator, metals, lipophilic molecules, hydrophilic molecules, ionic molecules (such as acidic and basic molecules), host molecule, dendrimer, polymers having affinity groups and other structures having specific affinity interactions with certain analyte. Through the binding between the binding moiety and the analyte, the non-covalent interaction between the charged affinity molecule and the specific analyte will give the resulting complex a detectable charge in ESI. In some embodiments one affinity moiety is coupled with multiple charged groups. In some embodiments multiple affinity moieties are coupled with one charged groups. In some embodiments multiple affinity moieties are coupled with multiple charged groups via linker/carrier.

Preferably, the charged groups are strongly ionizable groups such as tertiary amine or quaternary amine or guanidine for positive ions and phosphoric acid groups and sulphonic groups including sulfate and sulfonate for negative ions. It is desirable that these charged groups are permanently charged, e.g. quaternary amine or guanidine or phosphoric acid groups and sulphonic groups. Permanently charged group has charge in neutral condition, therefore provides the best ionization capability in ESI. In some embodiments the quaternary amine has four alkyl group substitutions such as methyl, ethyl or propyl substitutions. In some embodiments the quaternary amine has four aryl group substitutions. In some embodiments the quaternary amine has four substitutions consisting of the combination of aryl group and alkyl group. In some embodiments the charged group is conjugated directly to the affinity moiety. In other embodiments the changed group is part of the affinity moiety. Yet in another embodiment the affinity moiety is coupled to the charged group though a linker or a spacer.

The resulting ion detected by ESI will be that of the analyte plus the charged affinity molecule. It is possible that one analyte molecule can bind with multiple charged affinity molecules or multiple analyte molecules will bind with one charged affinity molecule or multiple charged affinity molecules bind with multiple analyte molecules, depending on how many binding sites each analyte molecule and each charged affinity molecule have. The resulting bound complex may contain multiple analyte molecules/charged affinity molecules. The detected molecular weight will be the sum of those from the analyte molecule (may be multiple) and the charged affinity molecule (may be multiple) in each formed complex. Because the ions in ESI sometimes carry multiple charges, one may also see m/z (mass-to-charge ratio) at half, 1/3 and 1/n molecular weight (n is the charge number). Sometime in the complex formed water molecule (or other solvent if used) and/or salt is also included, so the molecular weight also include these adduct.

One can readily introduce charged group into affinity molecules with chemical synthesis. For example, an affinity molecule having a —$NH_2$ group can react with $CH_3I$ to generate a $(CH_3)_3N^+$— in the affinity molecule, resulting in a permanently charged affinity molecule. An antibody can react with $(CH_3)_3N^+$—$CH_2$—COOH using EDC (1-Ethyl-3-(3-dimethylaminopropyl) carbodiimide) as coupling reagent to form an amide bond linkage with its —$NH_2$ group, or react with $(CH_3)_3N^+$—$CH_2$—$NH_2$ to couple with its —COOH group. Affinity molecules having —OH group such as cyclodextrin can also couple with $(CH_3)_3N^+$—$CH_2$—COOH via ester bond to gain a charged group. The detailed procedure for chemical coupling/organic synthesis/molecule derivatization can be adopted easily from literatures. However the affinity molecule should retain its binding activity after the modification. Therefore in some embodiments the disclosed method to detect analyte molecules using electrospray ionization (ESI) mass spectrometry comprise: providing affinity molecule having affinity moiety that can bind with said analyte molecule via a non-covalent or covalent bond; introducing charged group to the said affinity group to form a charged affinity molecule; mixing said charged affinity molecules with a sample solution containing said analyte to form a solution containing a covalently bound complex or noncovalently bound complex between said analyte and said charged affinity molecule; performing electrospray ionization (ESI) mass spectrometry for the solution containing the bound complex, and detecting the presence of the analyte by detecting the presence of the bound complex in mass spectrometry.

The analyte suitable for the current invention include small molecules, macromolecules as well as microorganism such as bacterial and virus. It is known that whole virus can be detected with ESI. One can also mix the sample containing the virus with the charged affinity molecule specific to the virus surface structure (e.g. highly positively charged antibody specific to virus surface protein) and then apply it to the ESI spectrometer for mass spectrometry analysis. The detected mass will be from an adduct of virus with the charged affinity molecule. Alternatively, the microorganism can be lysed first (either with physical method such as homogenizing or sonication; or with chemical lyse reagent such as detergent or biological reagent such as lysozyme) and then mixed with the charged affinity molecule specific to the released microorganism component (e.g. certain protein) and then apply it to the ESI for mass spectrometry analysis. The detected mass will be that of adduct of certain component with the charged affinity molecule. If the expected adduct is shown then the target microorganism is in the sample. One can also compare the mass spectra of those before and after adding the charged affinity molecule, if the mass spectrum pattern (e.g. appearance of new peaks) is changed besides the peaks of the charged affinity molecule, the target microorganism is present. Multiple charged affinity molecules (e.g. multiple charged antibodies specific to multiple antigens) can also be applied.

Figure 7:
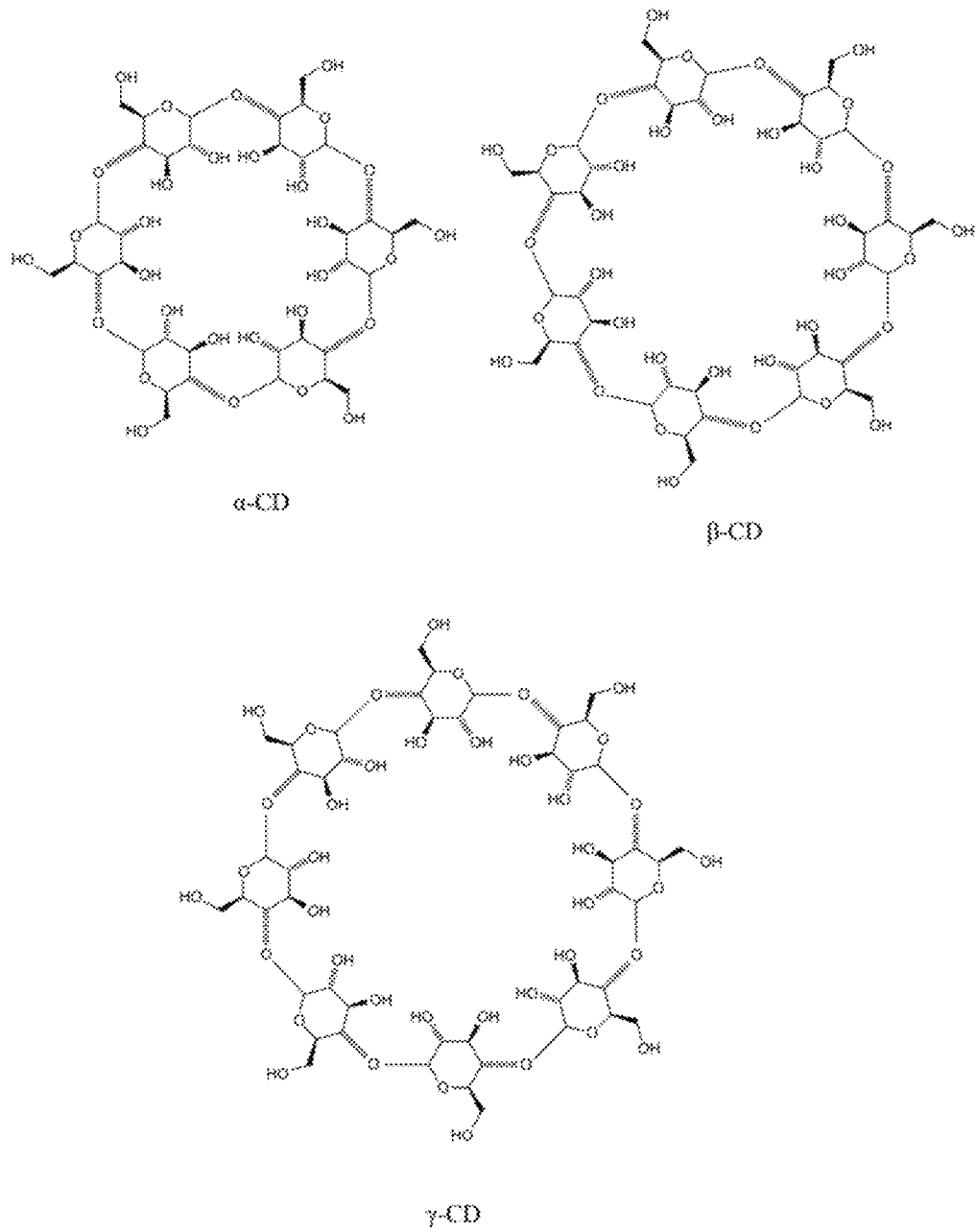
FIG. 7 shows structures of un-modified cyclodextrin without charge.
Figure 8:
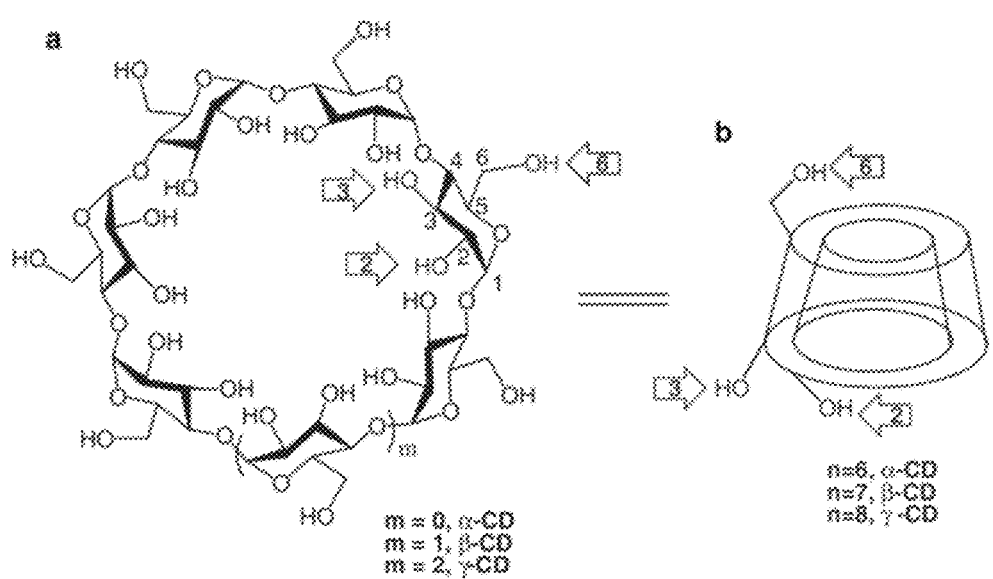
FIG. 8 shows examples of potential modification sites of cyclodextrin to introducing charged group.
Figure 9:
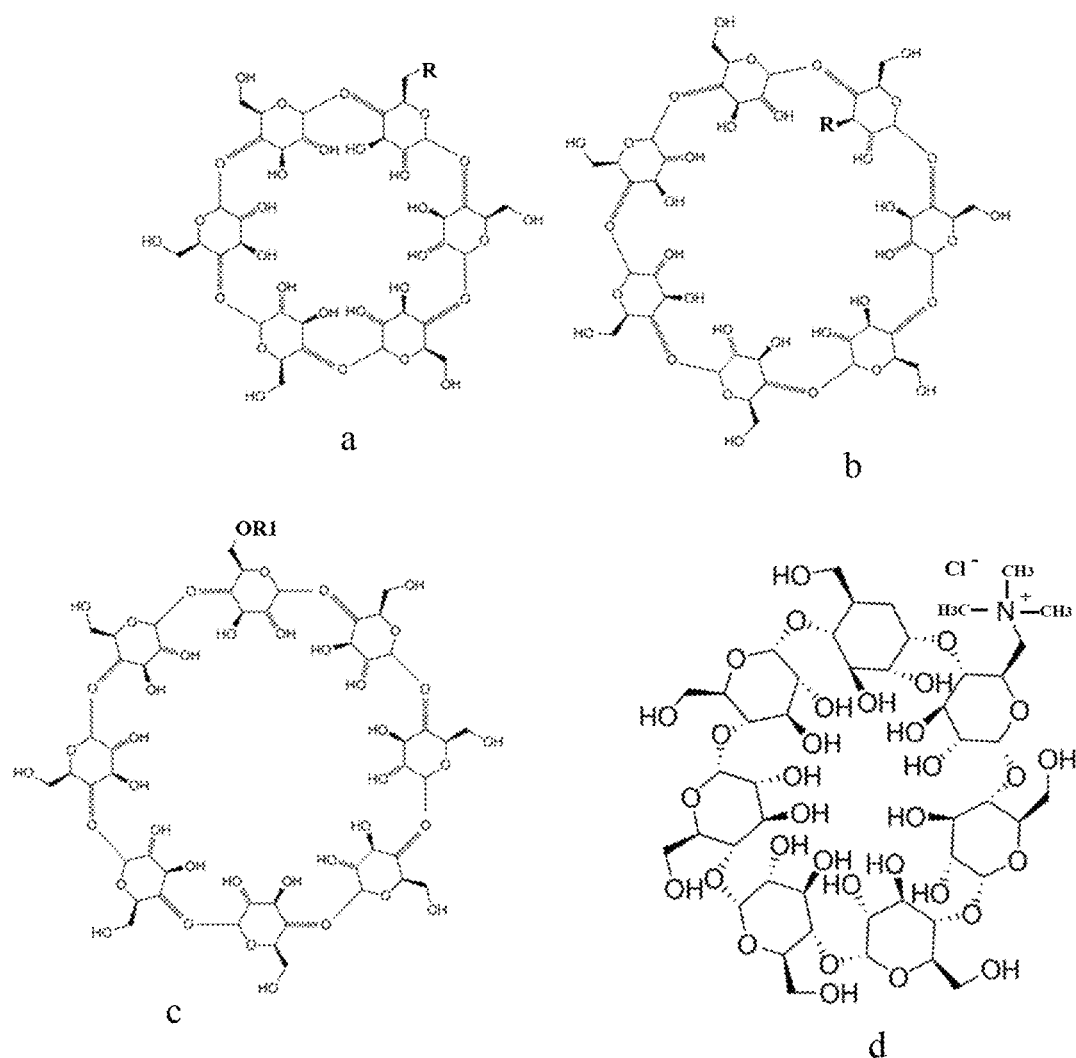
FIG. 9 shows examples of cyclodextrin modified to introduce one charged group.
Figure 10:
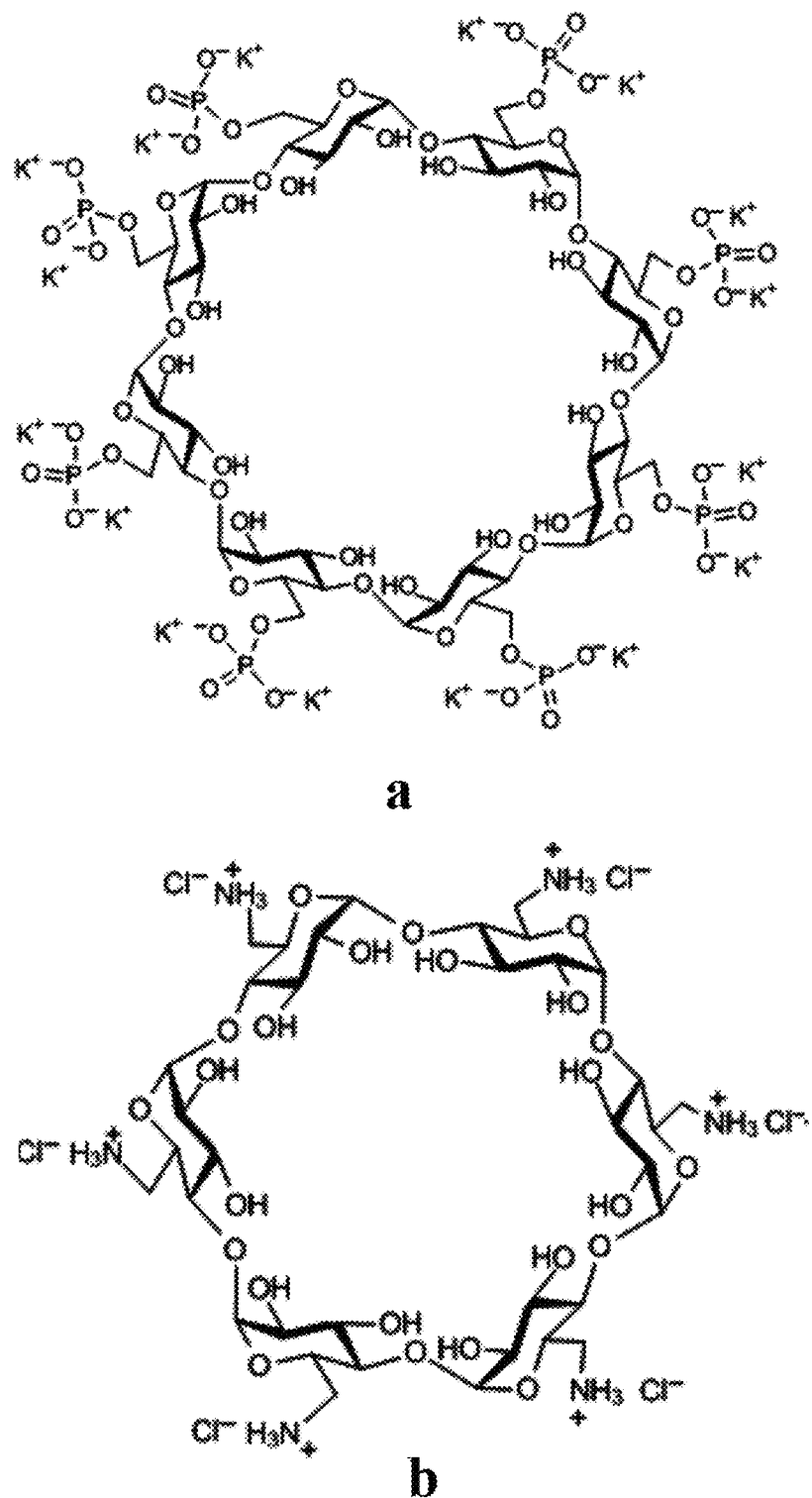
FIG. 10 shows examples of modified cyclodextrin having multiple charged groups.
Figure 11:
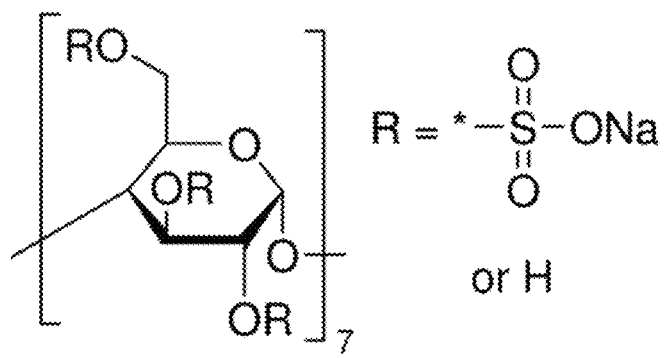
FIG. 11 shows the structure of a beta-cyclodextrin sulfate.
Figure 12:
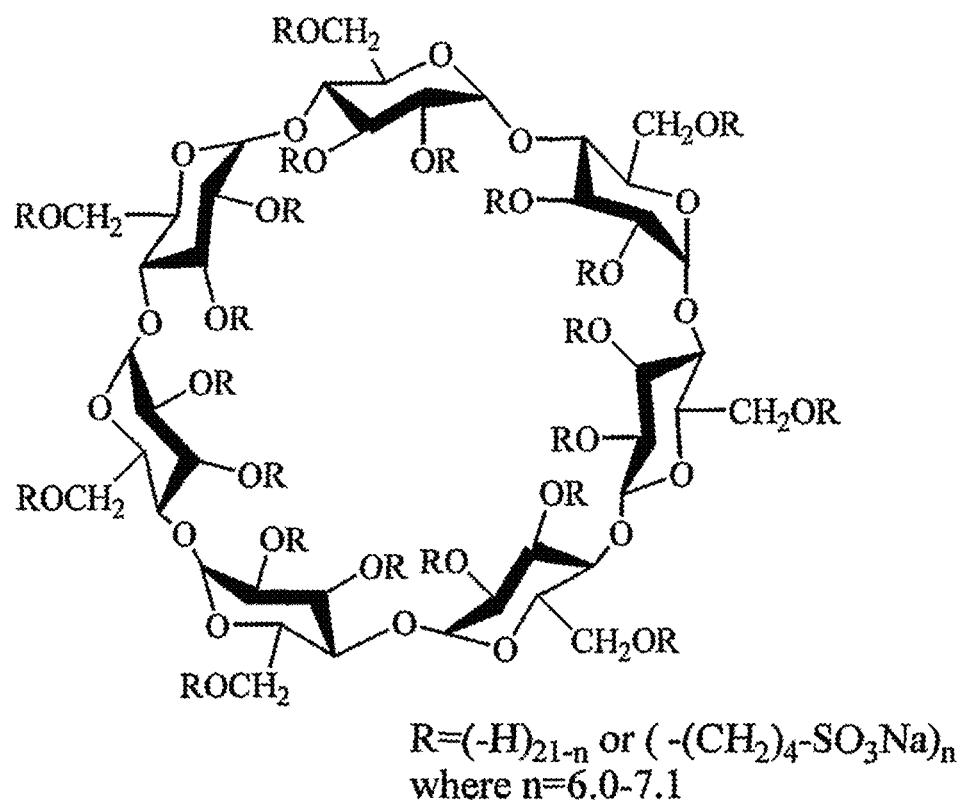
FIG. 12 shows the structure of Captisol.
Figure 13:
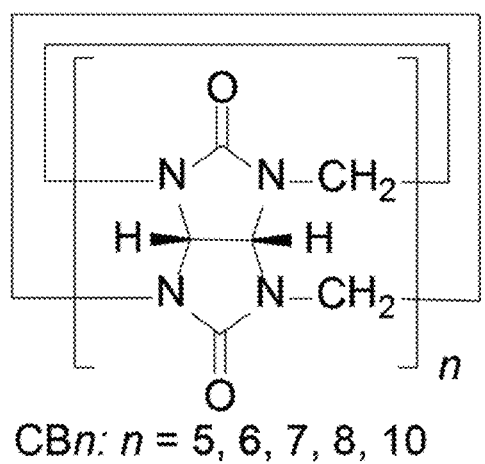
FIG. 13 shows structures of un-modified cucurbituril without charge.
Figure 14:
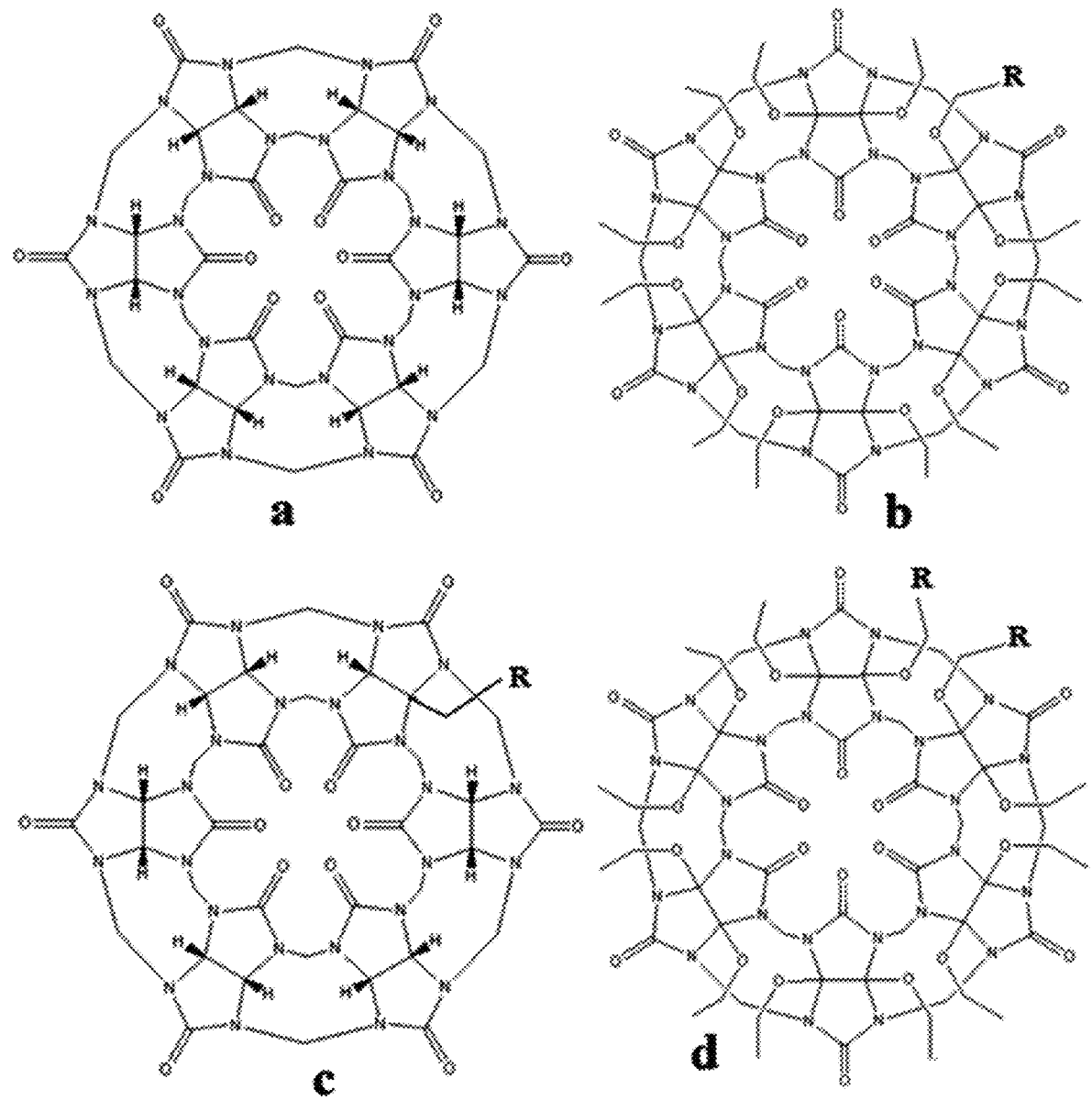
FIG. 14 shows structures of example of un-modified cucurbit[6]uril and modified cucurbit[6]uril to introduce charged group.
Figure 15:
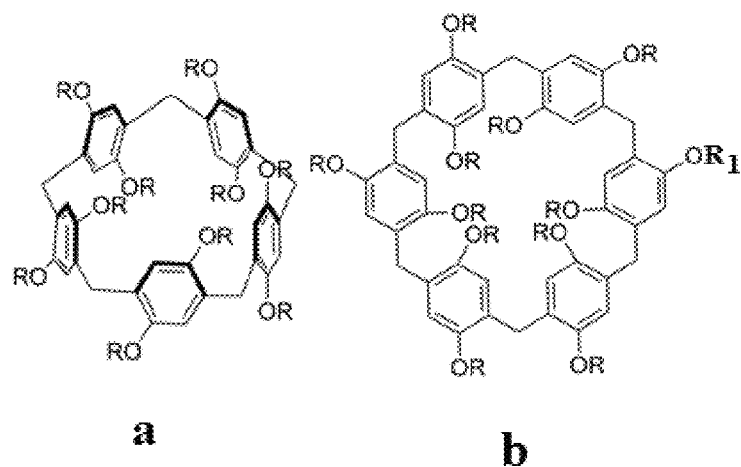
FIG. 15 shows structures of example of pillar[5]arene and pillar[6]arene.
Figure 16:
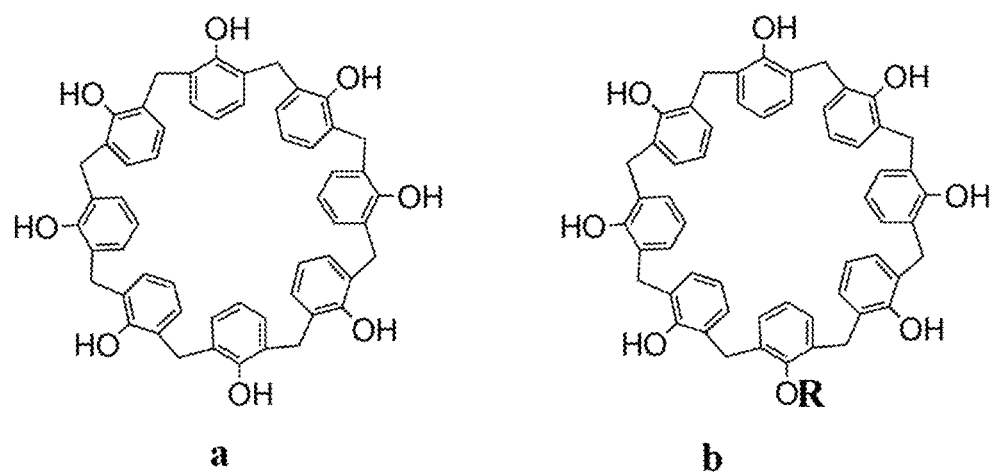
FIG. 16 shows structures of example of un-modified calix[8]arene and modified calix[8]arene.
Figure 17:
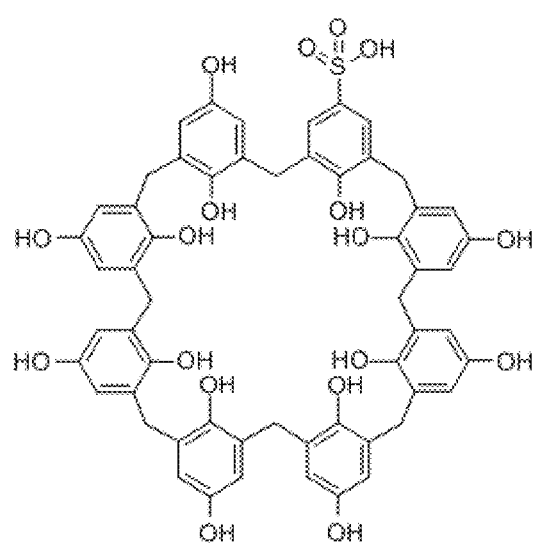
FIG. 17 shows structure of example of calix[8]arene sulfonate.
Figure 18:
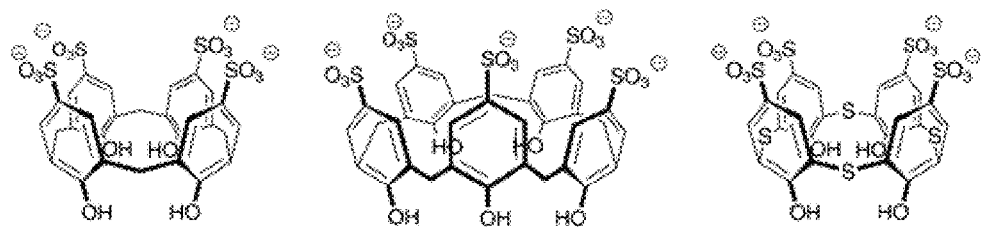
FIG. 18 shows structures of calixarene sulfonate of different ring size.
Figure 18:
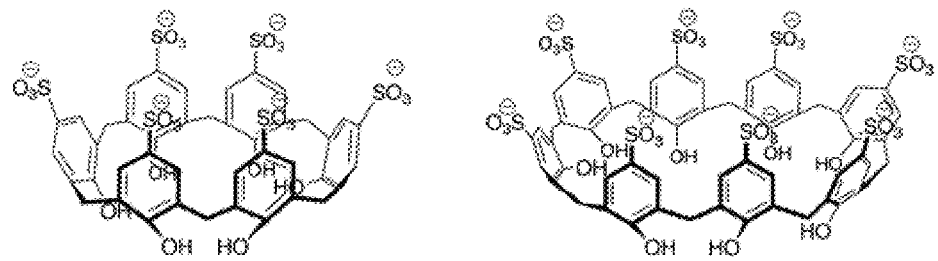
Figure 19:
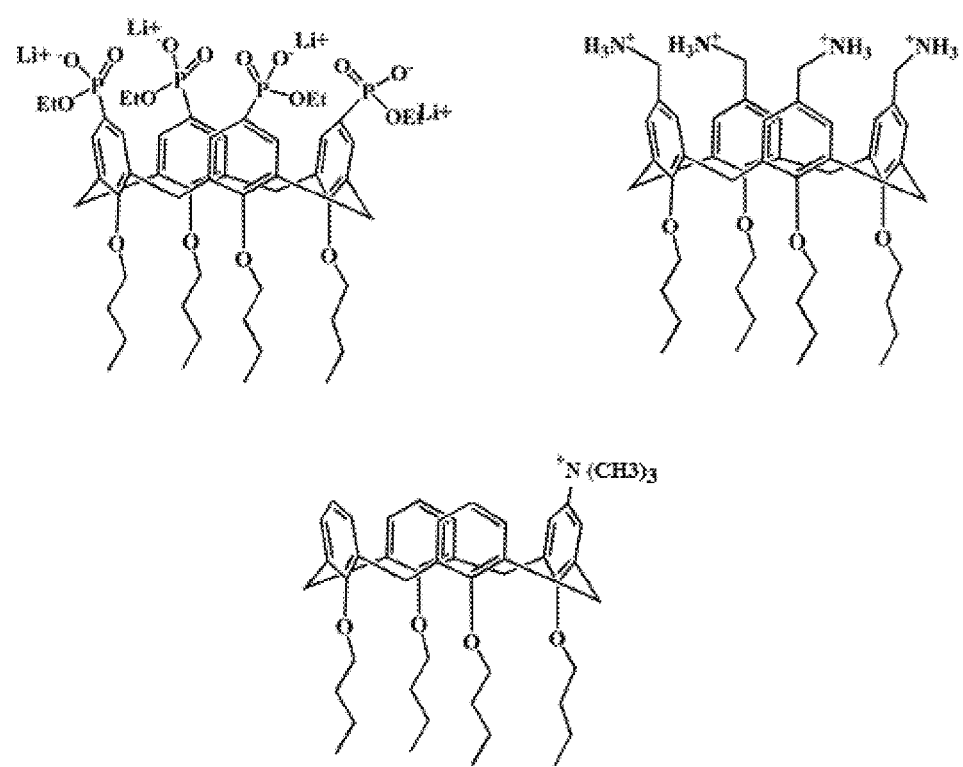
FIG. 19 shows examples of charged calixarene derivatives.

The host molecule used in host-guest chemistry is suitable for the current invention, which can be used as affinity molecules. They include but not limited to cyclodextrin, calixarene, pillararene, cucurbituril and their analogues or derivatives. They can be introduced with charged group easily via chemical bonds such as ester bond, amide bind, C—C bond, C—N bond and etc. FIGS. 7-19 showed examples of these host molecules and their charged derivatives suitable for the current application. They can bind with non-ionizable analyte molecule or difficult to ionize analyte molecule to form a charged complex to improve the detection of these analyte in ESI. FIG. 7 shows structures of un-modified cyclodextrin without charge include alpha, beta and gamma cyclodextrin. They can be readily derivatized to have charged groups at 2, 3 or 6 position as shown in FIG. 8. FIG. 9 shows examples of cyclodextrin modified to introduce one charged group, in which R can be a quaternary amine or guanidino group such as —$CH_2$—$N^+(CH_3)_3$ and R1 can be a sulfate group. FIG. 10 shows examples of modified cyclodextrin having multiple charged groups including either negative charged groups or positive charged groups. FIG. 11 shows the general structure of a beta-cyclodextrin sulfate. FIG. 12 shows the structure of beta-cyclodextrin sulfonate, which is captisol. FIG. 13 shows structures of un-modified cucurbituril, which has no permanent charge. FIG. 14a shows structures of example of un-modified cucurbit[6]uril. FIG. 14b,c,d show structures of example of modified cucurbit[6]uril, in which R can be a charged group such as quaternary amine, guanidine or sulfonate groups. FIG. 15 shows structures of example of pillar[5]arene and pillar[6]arene. When R=H and R1 is charged group, FIG. 15a is unmodified pillar[5]arene and FIG. 15b is unmodified pillar[6]arene having charge. FIG. 16 shows structures of example of un-modified calix[8]arene and modified calix[8]arene, in which R can be a charged group such as sulfate or quaternary amine. FIG. 17 shows structure of a calix[8]arene sulfonate. FIG. 18 shows structures of calixarene sulfonate of different ring size, which having multiple negative charged groups. FIG. 19 shows examples of charged calixarene derivatives.

Example 1

A DHB like molecule (photon absorbing moiety) is coupled with a lipophilic long alkyl chain (affinity moiety), therefore has affinity for lipophilic compounds (FIG. 1). This affinity matrix could selectively desorb/ionize lipophilic analyte in a mixture for MALDI mass analysis. Using this affinity matrix as matrix and standard MALDI analysis protocol (protocol available from Mass Spectrometry for Biotechnology; Gary Siuzdak, Academic Press 1996), a sample containing a mixture of dynorphin A-(1-11) and more lipophilic acetylated dynorphin A-(1-11) at 1:1 ratio gave 10 times higher peak of acetylated dynorphin A-(1-11) than the peak of less lipophilic dynorphin A-(1-11) while using DHB as matrix gave almost same peak height for two analytes. This enhanced signal of acetylated dynorphin A-(1-11) indicates the selective desorption/ionization capability of the lipophilic affinity matrix. The typical mixing and incubation time is several minutes. Longer incubation time can result in more complete binding. The affinity moiety is not limited to alkyl chain, for example, if the affinity moiety is biotin instead of the long alkyl chain, the resulting affinity matrix can be used to selectively desorb/ionize avidin or streptavidin.

Example 2

Figure 2:
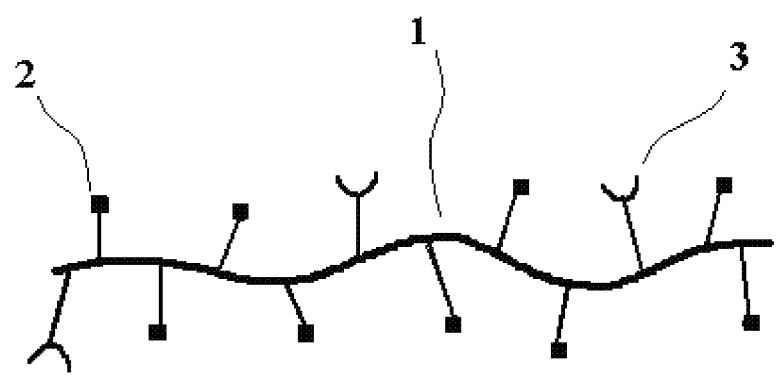
FIG. 2 shows another example of the polymer based selective affinity matrix.

FIG. 2 shows a polymer having both affinity groups and photon energy absorbing groups covalently coupled with it. The polymer 1 is polylysine (MW=20,000), the photon energy absorbing groups 2 are alpha-cyano-4-hydroxycinnamic acid (CCA) molecules and the affinity groups 3 are antibodies. The CCA and antibodies are coupled to the side chains of polylysine via amide bonds. The preferred ratio of antibody to CCA is 1:5 to 1:20. This polymer can be used as a selective affinity matrix to selectively desorb/ionize the corresponding antigen in MALDI analysis. A further modification of this affinity matrix is that the affinity groups are covalently linked to the polymer back bone while the photon energy absorbing groups are bounded to the polymer by non-covalent interaction such as ion pairing or lipophilic interaction.

Example 3

Figure 3:
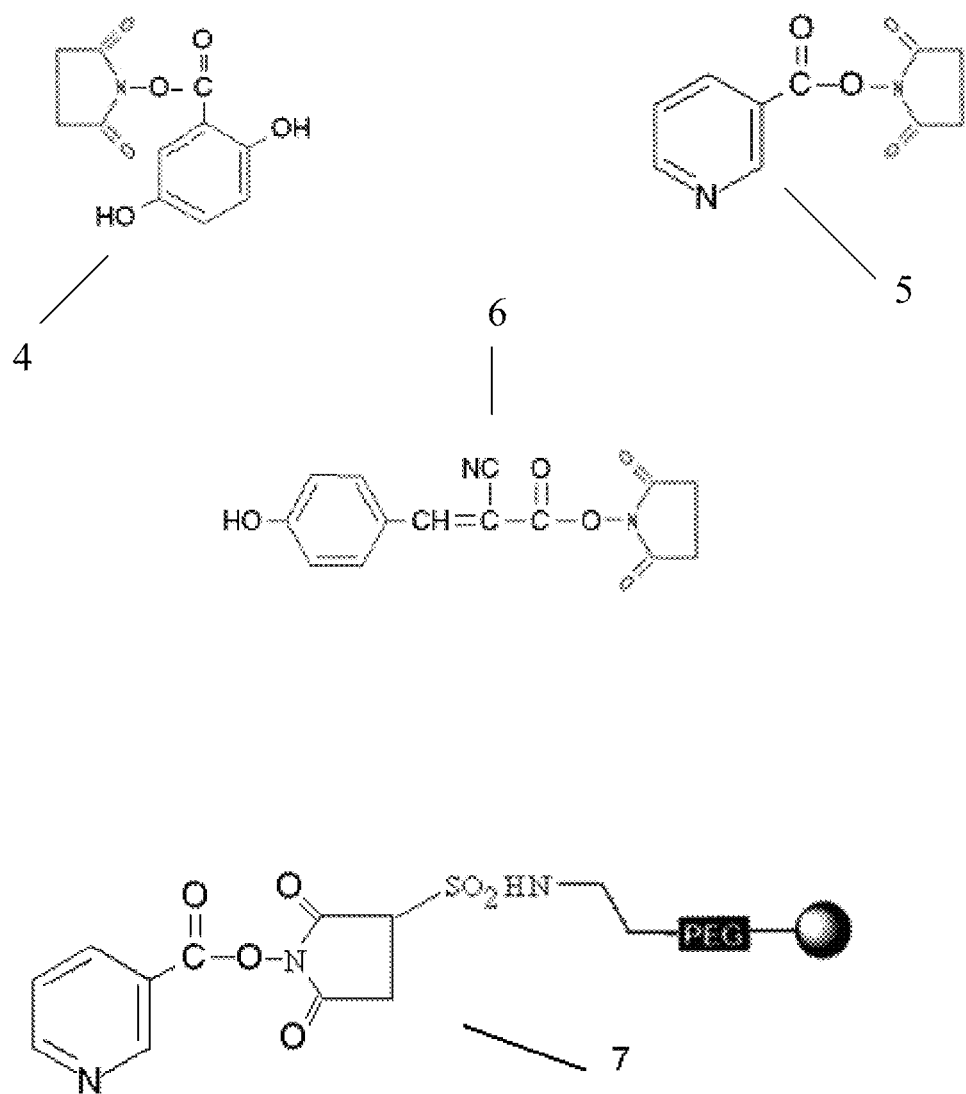
FIG. 3 shows examples of reactive matrix.

FIG. 3 shows the examples of several reactive matrix molecules: 2,5-dihydroxybenzoic acid (DHB)-NHS ester, alpha-cyano-4-hydroxycinnamic acid (CCA)-NHS ester and 3-picolinic acid-NETS ester. The DHB-NHS ester 4, 3-Picolinic acid-NHS ester 5 and CCA-NHS ester 6 are active esters of known matrix DHB, CCA and 3-Picolinic acid respectively. They can react with the analyte molecules containing free amine groups upon mixing and incubation in sample solution. Preferred incubation time is 10~60 minutes. Using these reactive matrix molecules as matrix and standard MALDI analysis protocol, the analyte containing amine groups can be readily detected in MALDI analysis. Reactive matrix can also be immobilized on solid phase support such as the structure 7 in the figure, in structure 7, the 4, 3-picolinic acid-NETS ester is immobilized on a PEG resin (Nova biochem), therefore allow easy purification of unreacted matrix.

Example 4

Figure 4:
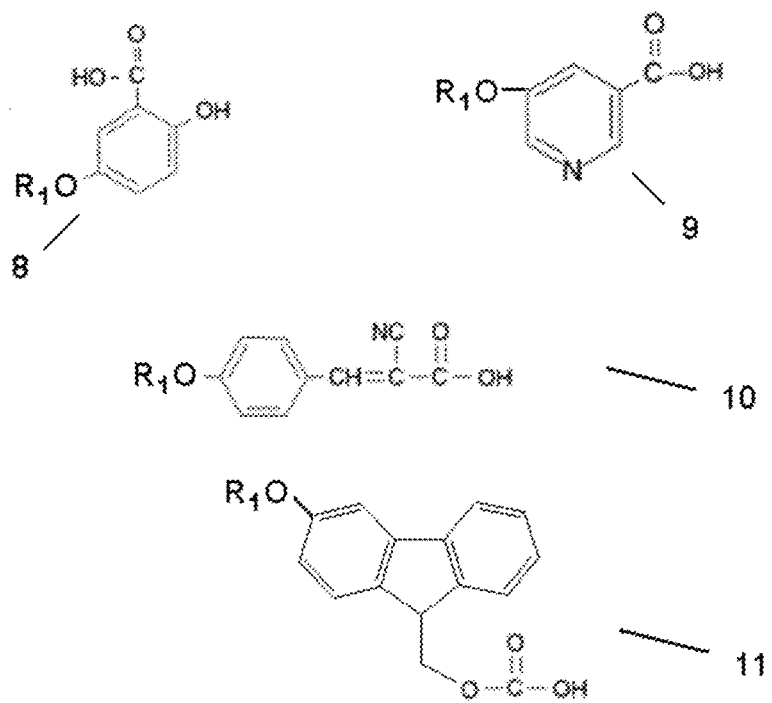
FIG. 4 shows examples of matrix carrying charged groups.

FIG. 4 shows examples of several charged matrix molecules, R1 is a charged group such as $(CH_3)_3N^+$—$CH_2$— or $(CH_3)_2N$—$CH_2CH_2$—, R1 can also be other charged groups as long as it provides a strong ionizable groups which inclues but not limited to hetero cycles, alkyl amines and etc. 8,9,10 are 2,5-dihydroxybenzoic acid (DHB), 3-picolinic acid and alpha-cyano-4-hydroxycinnamic acid (CCA) derivatives respectively. 11 is a Fmoc derivatives. Fmoc is s strong UV absorbing group. Further more, the photon absorbing moieties in FIG. 4 are not limited to the structure listed within, they can be any chemical groups as long as they have strong photon absorbing after they coupled with the analyte. These four charged matrix molecules can react with the analyte molecules containing free amine groups upon mixing and incubation in sample solution at the presence of coupling reagent. The solution can be either water based or organic solvent such as DMSO. Preferred incubation time is 10~60 minutes. Using these charged matrix molecules as matrix and standard MALDI analysis protocol; the analyte containing amine groups can be readily detected in MALDI analysis. In one embodiment, 5 mg of charged reactive matrix selected from 8,9,10 and 11 is mixed with 1 mg of avidin, an amine group containing protein in 0.1M PBS and 2 mg of EDC ((1-ethyl-3-(3-dimethyllaminopropyl) carbodiimide) for 30 min, next a drop of the mix is applied to the MALDI chip with a drop of 1% DHB aqueous solution, after drying, the MALDI analysis is performed, the peak shown has the molecular weight of avidin plus the matrix minus the leaving group during the coupling.

Example 5

Figure 5:
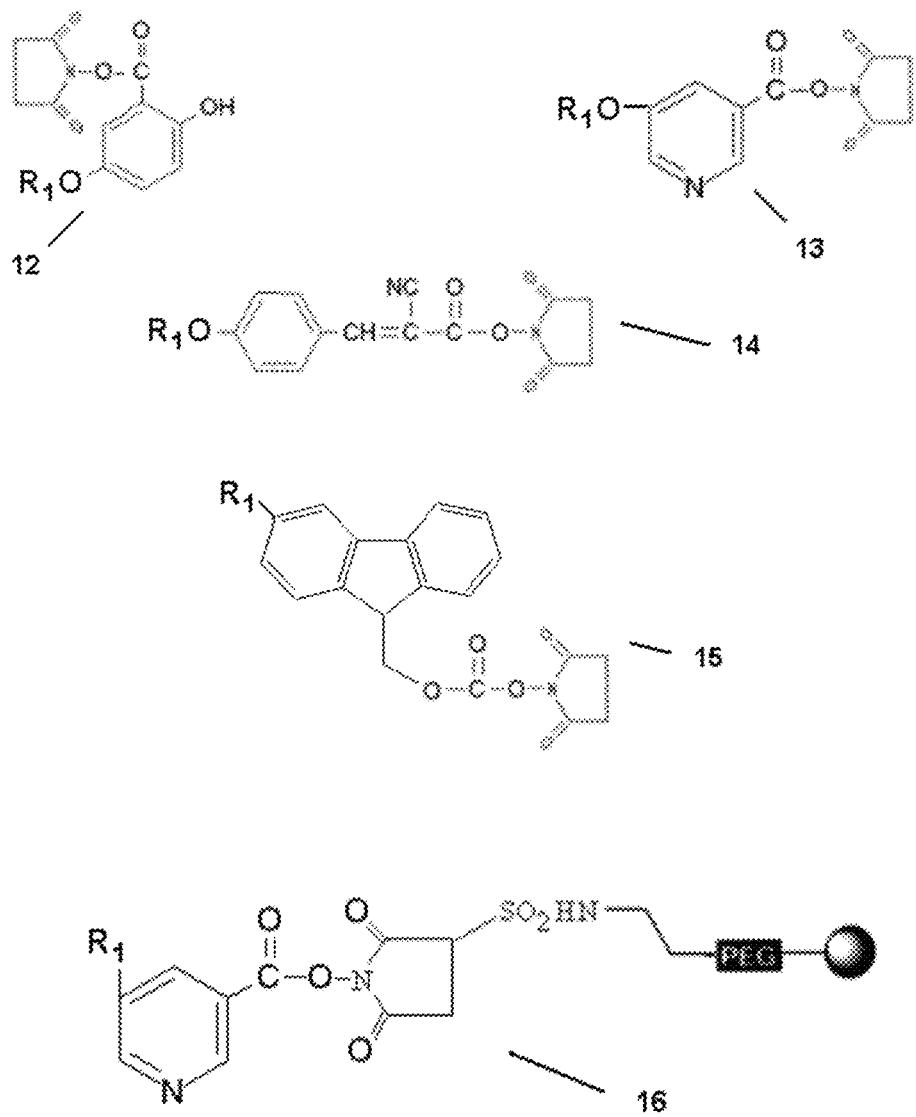
FIG. 5 shows examples of reactive matrix carrying charged groups in NHS ester form.

FIG. 5 shows examples of several charged reactive matrix molecules, $R_1$ is a charged group such as $(CH_3)_3N^+$—$CH_2$— or $(CH_3)_2N$—$CH_2CH_2$—, $R_1$ can also be other charged groups as long as it provide a strong ionizable groups which inclue but not limited to hetero cycles, alkyl amines and etc. 12,13 and 14 are charged derivatives of 2,5-dihydroxybenzoic acid (DHB)-NHS ester, 3-picolinic acid-NETS ester and alpha-cyano-4-hydroxycinnamic acid (CCA)-NHS ester respectively. 15 is a Fmoc —NHS ester derivatives. Fmoc is s strong UV absorbing group. Further more, the photon absorbing moieties in FIG. 5 are not limited to the structure listed within, they can be any chemical groups as long as they have strong photon absorbing after they coupled with the analyte. These four charged reactive matrix molecules can react with the analyte molecules containing free amine groups upon mixing and incubation in sample solution. The solution can be either water based or organic solvent such as DMSO. Preferred incubation time is 10~60 minutes. Using these charged reactive matrix molecules as matrix and standard MALDI analysis protocol, the analyte containing amine groups can be readily detected in MALDI analysis. In one embodiment, 2 mg of charged reactive matrix selected from 12-15 is mixed with 1 mg of benzylamine in DMSO for 5 min, next a drop of the mix is applied to the MALDI chip with or without the addition of a drop of 5% DHB ethyl alcohol solution, after drying, the MALDI analysis is performed, the peak shown has the molecular weight of benzylamine plus reactive matrix minus the leaving group during the coupling (NHS group and $H_2O$). In structure 16, the 4, 3-picolinic acid-NHS ester is immobilized on a PEG resin (Nova biochem), therefore allow easy purification of unreacted matrix. The resin can be removed from the coupling product before MALDI analysis. Similarly, the non-charged reactive matrix molecules in FIG. 3 can also be used instead.

Example 6

Figure 6:
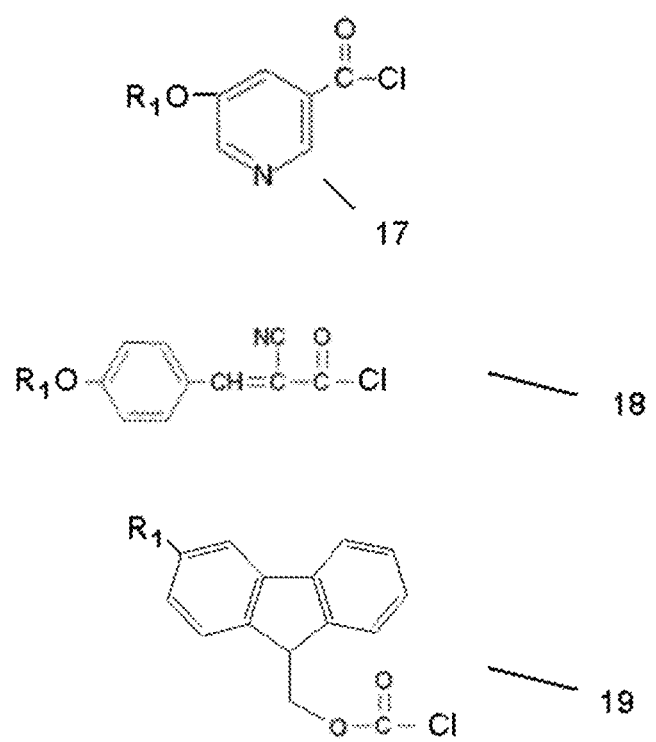
FIG. 6 shows examples of matrix carrying charged groups in acid chloride form.

FIG. 6 shows examples of several charged matrix molecules, $R_1$ is a charged group such as $(CH_3)_3N^+$— or $(CH_3)_2N$—$CH_2CH_2$—, $R_1$ can also be other charged groups as long as it provide a strong ionizable groups which include but not limited to hetero cycles, alkyl amines and etc. 17 and 18 are charged derivatives of 3-picolinic acid chloride and alpha-cyano-4-hydroxycinnamic acid (CCA) chloride respectively. 19 is a Fmoc chloride derivatives. These three charged matrix molecules can react with the analyte molecules containing free amine groups or —OH groups or —SH groups upon mixing and incubation in sample solution. The solution can be organic solvent such as acetone, DMF or DMSO. Preferred incubation time is 2~20 minutes. Using these charged matrix molecules as matrix and standard MALDI analysis protocol, the analyte containing amine groups/—OH group/—SH groups can be readily detected in MALDI analysis. In one embodiment, 2 mg of charged reactive matrix selected from 17~19 is mixed with 1 mg of cyclodextrin, an —OH group containing carbohydrate in DMSO for 30 min, next a drop of the mix is applied to the MALDI chip with/without the addition of a drop of 5% DHB ethyl alcohol solution, after drying, the MALDI analysis is performed, the peak shown has the molecular weight of cyclodextrin plus the matrix minus the leaving group during the coupling.

Example 7

The product in example 4 is a charged matrix-avidin covalent complex. This product is indeed an affinity matrix that can be used to detect its binding partner biotin. In one embodiment, 1 mg of purified charged affinity matrix-avidin is mixed with 10 ug of biotin in 100 ul 0.01 M PBS for 15 min, next a drop of the mix is applied to the MALDI chip with/without a drop of pH neutralized 1% CCA solution, after drying, the MALDI analysis is performed, the peak shown has the molecular weight of affinity matrix avidin plus biotin.

Example 8

Biotin is a small molecule that can bind with streptavidin tightly. Charged group R such as $(CH_3)_3N^+$—$CH_2$—$NH_2$ can couple with the —COOH group of biotin generating amide bond using EDC to form a charged affinity molecule for streptavidin detection. In order to detect streptavidin with ESI, 1 ml $(CH_3)_3N^+$—$CH_2$—NH-Biotin aqueous concentration (0.001%~0.1%, 1 mM PBS buffer, which can be made by diluting 0.1M PBS buffer with water at 1:100 ratio), is mixed with 1 ml solution containing streptavidin aqueous solution, incubated for 3 min under room temperature, then injected to ESI device to measure its mass spectrometry. Upon mixing them together, the detection of streptavidin will be enhanced due to the formed charged biotin+streptavidin complex in ESI or MALDI. A non-acidic matrix is preferred if using MALDI as the mass spectrometry method. R can also be other charged groups as long as it provides a strong ionizable group which include but not limited to hetero cycles, alkyl amines and etc. The resulting ion for detection will be streptavidin+charged biotin. If this peak is shown in ESI, the streptavidin is present in the sample. Because each streptavidin can bind with 4 biotins, streptavidin+n biotin (n=1~4) peaks will be present depending on the ratio between streptavidin and biotin.

Example 9

In this example, charged cyclodextrin is used as charged affinity molecule to help the detection of analyte molecules that can bind with cyclodextrin, especially if the analyte molecule is not charged. Cyclodextrin (CD) is a sugar molecule forming a ring (en.wikipedia.org/wiki/Cyclodextrin); there are many types of cyclodextrin such as:
α-cyclodextrin: six membered sugar ring molecule
β-cyclodextrin: seven sugar ring molecule
γ-cyclodextrin: eight sugar ring molecule.

These cyclodextrin can bind with many small molecules. For example, both β-cyclodextrin and methyl-β-cyclodextrin (MβCD) can bind with cholesterol. The methylated form MβCD (methyl-beta-cyclodextrin) was found to be more efficient than β-cyclodextrin. Cholesterol is a lipidic, waxy steroid as an uncharged molecule. It cannot be detected by traditional ESI since it has no charge. There are many types of charged cyclodextrin available, such as amino-cyclodextrin, those described in U.S. Pat. No. 5,959,089, 6-mono-amino-6-deoxy-α-cyclodextrin, 3-amino-cyclodextrin. Examples of 3-amino derivative of β-cyclodextrin ($CD_3NH_2$) and other charged cyclodextrin can be found in Journal of chromatography. B, Analytical technologies in J Chromatogr A. 2009 Apr. 24; 1216(17):3678-86. One can easily introduce a charged group on cyclodextrin by chemical modification.

In order to detect cholesterol with ESI, one can use the charged cyclodextrin described above (e.g. a CD from FIG. 9*d*) at a suitable aqueous concentration (e.g. 0.001%~0.5%, pH=5~7, 10 mM ammonium acetate buffer, pH=7), mix with the solution containing cholesterol aqueous or methanol/water 1:1 solution, pH=5-8), then analyze it using ESI. The ESI analysis procedure is well known to the skilled in the art. The molecule weight peak seen in the ESI is cholesterol+cyclodextrin. Other CD such as those described in FIGS. 10*a* and 10*b*, or Captisol or $CD_3NH_2$ can also be used instead. Other charged affinity ligand such as those described in Journal of Lipid Research Volume 40, 1999, 1475 (the amino derived cyclodextrin and cyclophane) can also be used to detect cholesterol in ESI as long as they can bind with cholesterol. This method can also be used in HPLC-ESI analysis (LC-MS) for cholesterol, the sample with cholesterol can either premixed with charged CD or the charged CD is added to the HPLC mobile phase instead (0.001%~0.1% in mobile phase). Cholesterol has no ionizable group therefore it cannot show $(M-H)^-$ or $(M+H)^+$ in ESI. The current method allows the detection of cholesterol by detecting the charged CD—cholesterol complex instead; therefore improve the detection of non-ionizable analyte in ESI.

In order to detect benzyl alcohol with ESI, 1 ml $CD_3NH_2$ or the CD in FIG. 9d aqueous solution (concentration at 0.001%~0.1%, 1 mM PBS buffer, pH=6 by adjusted it with 0.1M HCl), mix with 1 ml solution containing benzyl alcohol aqueous solution, then injected to ESI mass spectrometer to measure its mass spectrometry. This method can also be used in HPLC-ESI analysis (LC-MS) for cholesterol, the sample with cholesterol can either premixed with charged CD or the charged CD is added to the HPLC mobile phase instead (0.001%~0.1% in mobile phase). The molecule weight peak observed in ESI is benzyl alcohol+ cyclodextrin complex. The presence of this complex indicates the presence of benzyl alcohol analyte in the sample.

This method can also be used to detect other molecules (such as amino acid derivatives) as long as they can bind with the charged affinity ligand (such as charged cyclodextrin) in ESI for enhanced detection sensitivity especially if the target molecule has no charge or weak charge in ESI by itself. The affinity molecule in the charged affinity ligand is not limited to biotin or CD, any molecule having affinity to the target analyte to form a complex in ESI and can be added with charged group will also be suitable to use. In order to increase the charge intensity on these affinity ligands, tertiary or quaternary amine (e.g. $(CH_3)_3N^+$— or $CH_3)_2N^+$— groups) can be used instead of primary amine. Permanently charged quaternary amine or guanidine is preferred. This can be done easily by chemical synthesis. Sometimes the target analyte is also charged and has opposite charge group of the affinity ligand (e.g. —COOH group in analyte and —NH2 in the affinity ligand), the complex formed may have net zero charge. In this kind of case, two or more charged group can be introduced to the affinity ligand to keep the resulting complex has a net charge, e.g. introduce two amino groups on the CD. The affinity ligand can also be labeled with negative charged groups such as —COOH group instead of positive charged amino groups and in this case the ESI will detect the negative charged complex instead. Since the affinity ligand can be quite water soluble (e.g. CD), it can also help the ESI detection of the low solubility compound (e.g. cholesterol) since the formed complex will be more water-soluble than low solubility analyte. If CD is used, because plain CD without amino or acid group will also be partially deprotonated in basic condition (e.g. pH=9) therefore carry a negative charge, it can also be used for the detection of non charged compound such as cholesterol by adjusting the solution to high pH such as pH=9.

One skilled in the art will readily appreciate that the present invention is well adapted to carry out the objects and obtain the ends and advantages mentioned, as well as those inherent therein. The compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims.

Example 10

In order to detect human IgG in a sample using ESI, first the goat anti human IgG antibody is labeled with $(CH_3)_3N^+$—$CH_2$—COOH using EDC coupling to produce highly positively charged goat anti human IgG antibody and purified to remove the coupling reagents and unlabeled antibody using HPLC, next 1 ml 0.1 ug/ml said goat anti human IgG antibody in 10 mM ammonium acetate buffer, pH=7 is mixed with 1 ml sample and incubated for 3 min in room temperature. The sample is then loaded to ESI spectrometer for analysis. The presence of peaks from adduct of goat anti human IgG antibody with human IgG in the mass spectra indicate the presence of human IgG in the sample.

Example 11

In order to detect HIV virus in a sample using ESI, first the antibody against HIV gp120 (goat IgG) is labeled with $(CH_3)_3N^+$—$CH_2$—COOH using EDC coupling to produce highly positively charged antibody and purified to remove the coupling reagents and unlabeled antibody using HPLC, next 1 ml 0.1 ug/ml said antibody in 10 mM ammonium acetate buffer, pH=7 is mixed with 1 ml sample and incubate for 3 min in room temperature. The sample is then loaded to ESI spectrometer for analysis. The presence of peaks from adduct of antibody with virus particle in the mass spectra indicate the presence of HIV virus in the sample. Alternatively, 1 ml the sample can be mixed with 1 mg tween-20 and incubated for 5 min and then mixed with 1 ml 0.1 ug/ml said antibody in 10 mM ammonium acetate buffer, pH=7. The sample is then loaded to ESI spectrometer for analysis. The presence of peak from adduct of antibody with gp-120 in the mass spectra indicate the presence of HIV virus in the sample. Since the virus is lysed and the component inside is released, the marker inside the virus can also be used for detection. For example, HIV reverse transcriptase can be used instead of gp120 for HIV detection. In order to detect HIV virus in a sample using ESI, first the antibody against HIV reverse transcriptase (goat IgG) is labeled with $(CH_3)_3N^+$—$CH_2$—COOH using EDC coupling to produce highly positively charged antibody and purified to remove the coupling reagents and unlabeled antibody using HPLC, next 1 ml 0.1 ug/ml said antibody and 1 mg benzalkonium chloride in 10 mM ammonium acetate buffer, pH=7 mixed with 1 ml sample and incubated for 5 min in room temperature. The sample is then loaded to ESI spectrometer for analysis. The presence of peaks from adduct of antibody with HIV reverse transcriptase in the mass spectra indicate the presence of HIV virus in the sample.

Example 12

In order to detect *E coli* in a sample using ESI, the sample is divided into two parts. First the antibody (Goat polyclonal to *E. coli*, which is commercially available from many venders) against *E. coli* is labeled with $(CH_3)_3N^+$—$CH_2$—COOH using EDC coupling to produce highly positively charged antibody and purified to remove the coupling reagents and unlabeled antibody using HPLC, next 1 ml 0.1 ug/ml said antibody and 1 mg benzalkonium chloride in 10 mM ammonium acetate buffer, pH=7 is mixed with 1 ml sample and incubate for 10 min in room temperature. The sample is then loaded to ESI spectrometer for analysis. Another part of sample is treated the same except no antibody is added. This sample is then loaded to ESI spectrometer for analysis. The two spectra is compared, the difference (the change of the pattern of the peaks and newly appeared peaks except the antibody peaks) in the two spectrums indicate the presence of *E coli* in the sample.

Example 13

In order to detect benzyl acetate with ESI, 1 ml charged cucurbit[6]uril (FIG. 14d, R=$(CH_3)_3N^+$—$CH_2$—) aqueous solution (concentration at 0.001%~0.1%, 10 mM ammonium acetate buffer in 10% MeOH, pH=7), mix with 1 ml test sample containing benzyl acetate, then injected to ESI mass spectrometer to measure its mass spectrometry. This method can also be used in HPLC-ESI analysis (LC-MS) for benzyl acetate, the sample with benzyl acetate can either premixed with charged cucurbit[6]uril or the charged cucurbit[6]uril is added to the HPLC mobile phase instead (0.001%~0.1% in mobile phase). The molecule weight peak observed in ESI is benzyl acetate+cucurbit[6]uril complex. The presence of this complex indicates the presence of benzyl acetate in the sample.

Example 14

In order to detect benzyl acetate with ESI, 1 ml charged pillar[6]arene (FIG. 15b, R=H, R1 is sulfate) aqueous solution (concentration at 0.001%~0.1%, 10 mM ammonium acetate buffer in 10% MeOH, pH=7), mix with 1 ml test sample containing benzyl acetate, then injected to ESI mass spectrometer to measure its mass spectrometry. This method can also be used in HPLC-ESI analysis (LC-MS) for benzyl acetate, the sample with benzyl acetate can either premixed with charged pillar[6]arene or the charged pillar[6]arene is added to the HPLC mobile phase instead (0.001%~0.1% in mobile phase), in which case no pillar[6]arene is added to the sample before HPLC injection. The molecule weight peak observed in ESI is benzyl acetate+pillar[6]arene complex. The presence of this complex indicates the presence of benzyl acetate in the sample.

Example 15

In order to detect benzyl acetate with ESI, 1 ml calix[8]arene sulfonate (FIG. 17) aqueous solution (concentration at 0.001%~0.1%, 10 mM ammonium acetate buffer in 10% MeOH, pH=7), mix with 1 ml test sample containing benzyl acetate, then injected to ESI mass spectrometer to measure its mass spectrometry with the direct infusing mode. This method can also be used in HPLC-ESI analysis (LC-MS) for benzyl acetate, the sample with benzyl acetate can either premixed with calix[8]arene sulfonate or the calix[8]arene sulfonate is added to the HPLC mobile phase instead (0.001%~0.1% in mobile phase), in which case no calix[8]arene sulfonate is added to the sample before HPLC injection. The molecule weight peak observed in ESI is benzyl acetate+calix[8]arene sulfonate complex. The presence of this complex indicates the presence of benzyl acetate in the sample.

All patents and publications mentioned in this specification are indicative of the level of those skilled in the art to which the invention pertains. All patents and publications are herein incorporated by reference to the same extent as if each individual publication was specifically and individually indicated to be incorporated by reference. The inventions described above involve many well known chemistry, instruments, methods and skills. A skilled person can easily find the knowledge from text books such as the chemistry textbooks, scientific journal papers and other well known reference sources.

The invention claimed is:

1. A compound to improve the signal of non-ionizable analyte molecule that does not contain amine or acid group in electrospray ionization (ESI) mass spectrometry comprising a permanently charged motif and a binding motif selected from cucurbituril and pillararene that can bind with the said analyte molecule to form a non-covalent complex.

2. The compound according to claim 1, wherein the charged motif is a positively charged group.

3. The compound according to claim 1, wherein the charged motif is negatively charged group.

4. The compound according to claim 1, wherein the charged motif is a quaternary ammonium cation group.

5. The compound according to claim 1, wherein the charged motif is sulfate anion group.

* * * * *